United States Patent
Bolling et al.

(10) Patent No.: US 7,329,280 B2
(45) Date of Patent: Feb. 12, 2008

(54) METHODS OF IMPLANTING A MITRAL VALVE ANNULOPLASTY RING TO CORRECT MITRAL REGURGITATION

(75) Inventors: Steven F. Bolling, Ann Arbor, MI (US); Richard S. Rhee, Diamond Bar, CA (US)

(73) Assignee: Edwards Lifesciences Corp., Irvine, CA (US)

( * ) Notice: Subject to any disclaimer, the term of this patent is extended or adjusted under 35 U.S.C. 154(b) by 639 days.

(21) Appl. No.: 10/968,323

(22) Filed: Oct. 18, 2004

(65) Prior Publication Data
US 2005/0049698 A1    Mar. 3, 2005

Related U.S. Application Data

(63) Continuation of application No. 10/267,272, filed on Oct. 9, 2002, now Pat. No. 6,805,710.

(60) Provisional application No. 60/332,353, filed on Nov. 13, 2001.

(51) Int. Cl.
*A61F 2/24* (2006.01)
(52) U.S. Cl. ................... 623/2.36; 623/2.38
(58) Field of Classification Search ............ 623/2.36, 623/2.37, 2.38, 2.4
See application file for complete search history.

(56) References Cited

U.S. PATENT DOCUMENTS

| | | |
|---|---|---|
| 4,055,861 A | 11/1977 | Carpentier et al. |
| 5,104,407 A | 4/1992 | Lam et al. |
| 5,201,880 A | 4/1993 | Wright et al. |
| 5,258,021 A | 11/1993 | Duran |
| 5,450,860 A | 9/1995 | O'Connor |
| 5,607,471 A | 3/1997 | Seguin et al. |
| 5,824,069 A | 10/1998 | Lemole |

(Continued)

FOREIGN PATENT DOCUMENTS

EP    0 860 151    8/1998

(Continued)

OTHER PUBLICATIONS

IMR Redux—To Repair or Replace, Journal of Thoracic & Cardiovascular Surgery, Aug. 18, 2001.
Effect of Papillary Muscle Position on Mitral Valve, Function: Relationship to Homografts, The Society of Thoracic Surgeons Richard P. Cochran et al.; 1998.

(Continued)

*Primary Examiner*—Anhtuan T. Nguyen
*Assistant Examiner*—Christopher D Prone
(74) *Attorney, Agent, or Firm*—Rajiv Yadav; Guy Cumberbatch (57) ABSTRACT

Methods of implanting an annuloplasty ring to correct maladies of the mitral annulus that not only reshapes the annulus but also reconfigures the adjacent left ventricular muscle wall. A posterior portion of the ring rises or bows upward from adjacent sides to pull the posterior aspect of the native annulus farther up than its original, healthy shape. In doing so, the ring also pulls the ventricular wall upward which helps mitigate some of the effects of congestive heart failure. Further, one or both of the posterior and anterior portions of the ring may also bow inward. The methods include securing the annuloplasty ring with the anterior portion against the annulus anterior aspect and the posterior portion against the annulus posterior aspect so that the ring posterior portion elevates, and may also pull radially inward, the annulus posterior aspect and corrects the mitral regurgitation.

20 Claims, 9 Drawing Sheets

U.S. PATENT DOCUMENTS

| | | |
|---|---|---|
| 6,183,512 B1 | 2/2001 | Howanec, Jr. et al. |
| 6,187,040 B1 | 2/2001 | Wright |
| 6,231,602 B1 | 5/2001 | Carpentier et al. |
| 6,250,308 B1 | 6/2001 | Cox |
| 6,258,122 B1 | 7/2001 | Tweden et al. |
| 2001/0034551 A1 | 10/2001 | Cox |
| 2002/0173844 A1 | 11/2002 | Alfieri et al. |

FOREIGN PATENT DOCUMENTS

| | | |
|---|---|---|
| EP | 1 034 753 | 9/2000 |
| FR | 2 708 458 | 8/1993 |
| WO | WO 95/03757 | 2/1995 |
| WO | WO 01/19292 | 3/2001 |
| WO | WO 01/87191 | 11/2001 |

OTHER PUBLICATIONS

Atrioventricular Valve Repair Using Externally Adjustable Flexible Rings, The Journal of Thoracic and Cardiovascular pp. 1333-1337, surgery, Nov. 1995.

The Annals of Thoracic Surgery, pp. 368-369, vol. 46, No. 3, Sep. 1988.

Preliminary Experience in Mitral Valve Repair Using the cosgrove-Edwards Annuloplasty Ring, Giuseppe Gatti et al., Interactive Cardiovascular and Thoracic Surgery, vol. 2(3), pp. 256-261, 2003.

Effect of Annular shape on leaflet Curvature in Reducing Mitral leaflet Stree, Salgo et al., American Heart Association, Circulation 200;106:711.

MGH Study Shows Mitral Valve Prolapse Not a Stroke Risk Factor, Massachusetts General Hospial, pp. 1-3, Jun. 1999.

Techniques for 3D Quantitative Echocardiography, University of Washington Cardiovascular Research & Training Center Cardiac Imaging Research Lab, pp. 1-5, Oct. 2003.

Mitral Valve Reconstruction in the Patient with Heart Failure, Steven F. Bolling, heart Failure Reviews, 6, 177-185, 2001.

Surgical Alternatives for heart Failure, The Journal of Heart and Lung Transplant, Steven Bolling et al., 20, 729-733, 2001.

Mitral Valve Repair in Heart Failure, European Journal of Heart Failure, iva A. Smolens et al., 2 365-371, 2000.

METHODS OF IMPLANTING A MITRAL VALVE ANNULOPLASTY RING TO CORRECT MITRAL REGURGITATION

RELATED PATENT APPLICATION(S)

The present application is a continuation of U.S. application Ser. No. 10/267,272, filed Oct. 9, 2002, now U.S. Pat. No. 6,805,710 which claims priority under 35 U.S.C. §119(e) from Provisional Patent Application No. 60/332,353, filed Nov. 13, 2001, both entitled "Mitral Valve Annuloplasty Ring for Molding Left Ventricle Geometry," the disclosures of which are incorporated by reference herein in their entireties.

FIELD OF THE INVENTION

The present invention relates generally to medical devices, specifically to an annuloplasty ring and related procedure for surgically reconstructing and molding the mitral valve annulus of a patient's heart. More specifically, this invention relates to a mitral valve repair device and corresponding technique that involve over-correcting defects in the mitral valve annulus so as to remodel the left-ventricular geometric relationship.

BACKGROUND OF THE INVENTION

Congestive heart failure (CHF) is a leading cause of hospitalization and death in the United States, and its incidence is increasing. Secondary mitral regurgitation (MR), a complication of end-stage cardiomyopathy, refers to the backflow of blood from the left ventricle to the left atrium resulting from imperfections in the mitral valve. When the mitral valve allows blood to flow backward into the left atrium, the left ventricle must pump progressively harder to circulate blood throughout the body, which in turn promotes CHF. While heart transplantation is considered a standard treatment for select patients with severe CHF and end-stage heart disease, it is only applicable to a small percentage of patients because of the small number of available donor hearts and surgical risks for weaker patients. Accordingly, alternative medical and surgical strategies are evolving to treat such conditions.

Figure 1A:
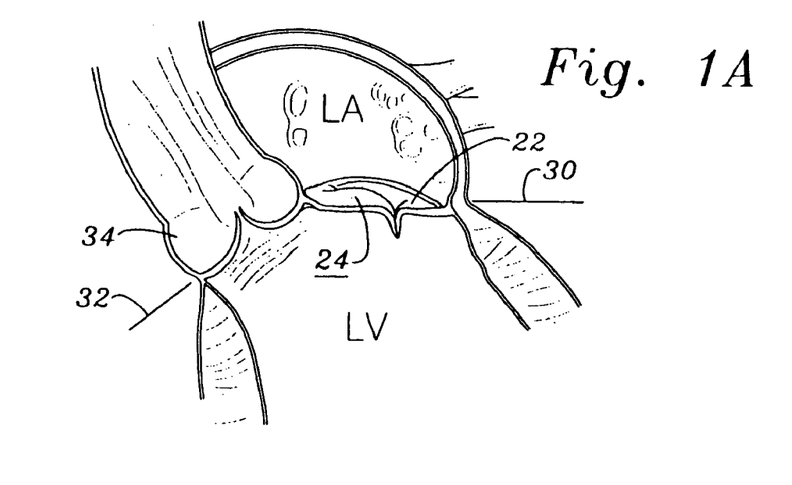
FIG. 1A is a cross-sectional view along an anterior-posterior plane through the left side of a heart illustrating healthy aortic and mitral valves and annuluses.
Figure 1B:
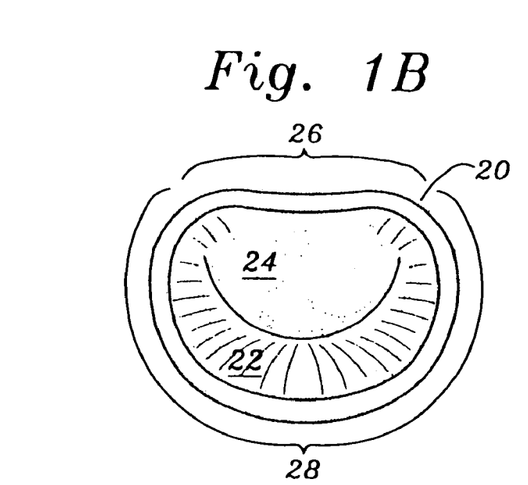
FIG. 1B is a plan view of a healthy mitral valve and annulus.

As seen in FIGS. 1A and 1B, the mitral annulus 20 represents the junction of the fibrous and muscular tissue that joins the left atrium LA and left ventricle LV. The average human mitral annular cross-sectional area is 5-11 $cm^2$. The mitral valve is a bicuspid valve having a large posterior leaflet 22 that coapts or meets with a smaller anterior leaflet 24. The anterior aspect 26 of the annulus, which is in continuity with the fibrous skeleton of the heart, has limited flexibility, whereas the posterior aspect 28 of the annulus, which is not attached to any rigid surrounding structures, has more flexibility. For the purpose of discussion, the mitral annulus 20 lies generally in a datum plane 30 (FIG. 1A) at an angle with respect to a datum plane 32 in which the aortic valve 34 is generally oriented. These datum planes 30, 32 can be defined as being perpendicular to the average blood flow through the respective valves. During systole the mitral annulus 20 assumes a generally elliptical shape as shown in FIG. 1B, and is able to contract and decrease in diameter, whereas, in diastole, it assumes a more circular shape and opens to permit blood to fill the left ventricle LV. Annular flexibility allows for increased leaflet coaptation during systole and increased annular orifice area during diastole.

Figure 2A:
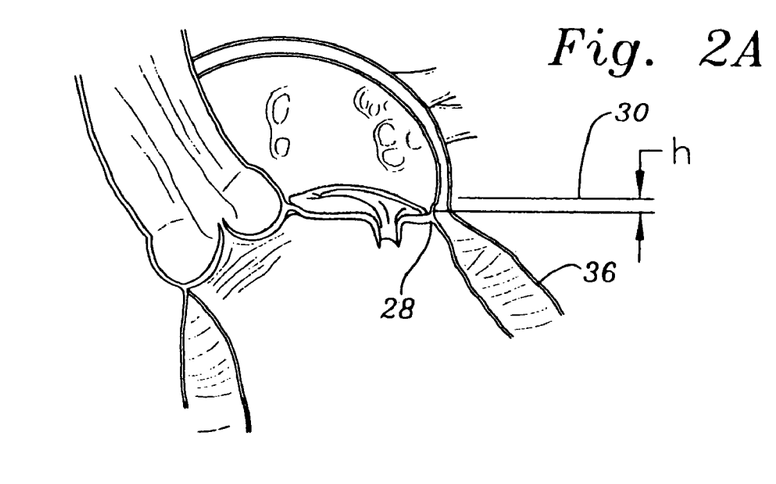
FIG. 2A is a cross-sectional view along an anterior-posterior plane through the left side of a heart illustrating a condition in the mitral valve that leads to mitral regurgitation (MR)
Figure 2B:
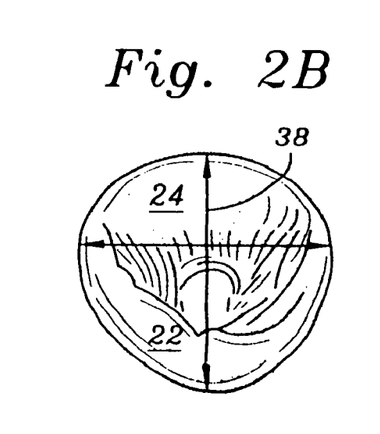
FIG. 2B is a plan view of the mitral valve of FIG. 2A.

In MR, dilation typically occurs along the more flexible posterior aspect 28 of the annulus, as seen in FIGS. 2A and 2B. Some patients experiencing a drop h of the posterior aspect 28 of the mitral valve annulus, as seen in FIG. 2A, and consequent relaxation of the posterior muscle wall 36 of the left ventricle LV. FIG. 2B illustrates the lengthening of the anterior-posterior dimension 38 and subsequent loss of coaptation between the posterior and anterior leaflets 22, 24.

MR leads to a cycle of continuing volume overload of the already dilated left ventricle LV, progression of annular dilation, increased left ventricle wall tension, increasing degrees of MR and worsening CHF. In MR, the regurgitant volume ejected into the left atrium LA is dependent upon mitral orifice size, ventricular/atrial pressure gradient and heart rate. The regurgitant flow into the left atrium LA increases left atrial pressure, which leads to atrial enlargement and an increase in compliance, and decreases forward systemic flow. Left atrial pressures rise during systole and decline in diastole.

Figure 3A:
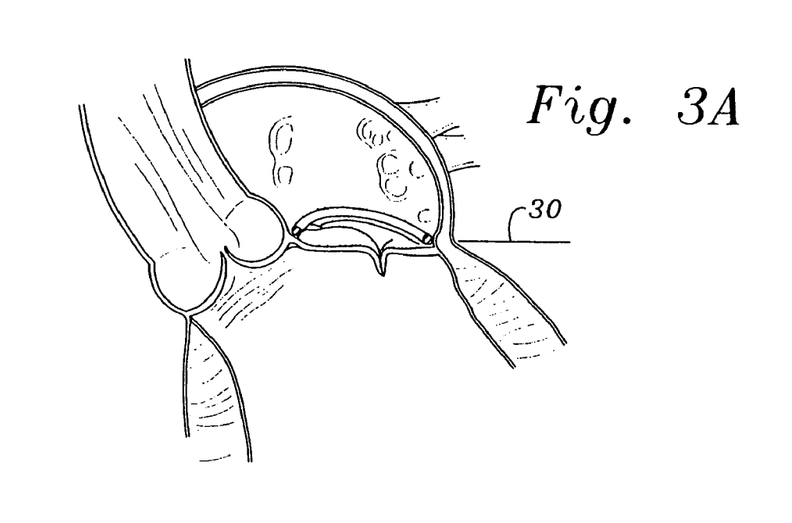
FIG. 3A is a cross-sectional view along an anterior-posterior plane through the left side of a heart illustrating the implantation of a conventional annuloplasty ring to restore the mitral valve to its healthy configuration.
Figure 3B:
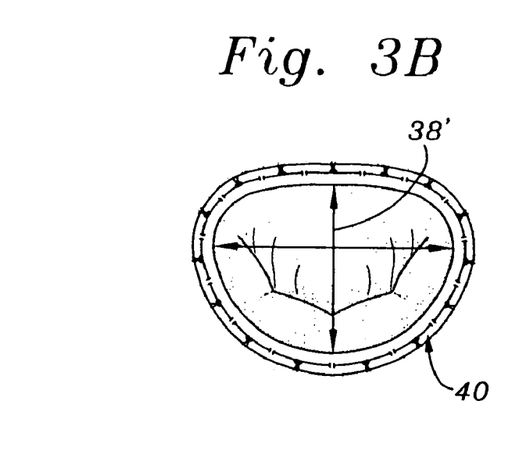
FIG. 3B is a plan view of the restored mitral valve of FIG. 3A.

FIGS. 3A and 3B illustrate the use of a Carpentier-Edwards PHYSIO annuloplasty ring 40 to restore the original healthy shape of the mitral annulus 20. The ring 40 is typically semi-rigid and planar and restores the primary anterior-posterior dimension 38' of the mitral annulus 20.

Various other interventions have been used to alter the size of the regurgitant orifice area. An increase in preload or afterload, or a decrease in contractility, results in dilation of the LV and an increase in regurgitant orifice area. The complex relationship between mitral annular area and leaflet coaptation may explain why some studies have found that performing a "valvular" repair, with an undersized flexible annuloplasty ring, has helped with a "muscular" problem of the left ventricle. For example, in a study conducted between 1993-1999 at the University of Michigan, 92 patients with end-stage cardiomyopathy and refractory MR underwent mitral valve repair with an "undersized" annuloplasty rings having a circumference smaller than that of the patient's annulus in its natural, pre-diseased state.

Annuloplasty rings have also been developed in various shapes and configurations over the years in an effort to correct MR and other conditions which reduce the functioning of the valve. For example, Carpentier, et al. in U.S. Pat. No. 4,055,861 disclosed two semi-rigid supports for heart valves, one of which being closed (or D-shaped) and the other being open (or C-shaped). In the closed configuration, the ring is generally flat about an anterior-posterior plane, and has a convex posterior side and a generally straight anterior side. U.S. Pat. Nos. 5,104,407, 5,201,880, and 5,607,471 disclose closed annuloplasty rings that are bowed slightly upward on their anterior side. Because the anterior aspect 26 of the mitral annulus is fibrous and thus relatively inflexible (at least in comparison to the posterior aspect 28), the upward curve in the anterior side of each ring conforms the ring more closely to the anatomical contour of the mitral annulus, and thus reduces undue deformation of the annulus.

It should be noted here that correction of the aortic annulus requires a considerably different ring then with a mitral annulus. For example, U.S. Pat. Nos. 5,258,021 and 6,231,602 disclose sinusoidal or so-called "scalloped" annuloplasty rings that follow the up-and-down shape of the three cusp aortic annulus. Such rings would not be suitable for correcting a bicuspid valve deficiency.

While good results in the treatment of CHF and MR have been obtained in the preliminary applications of the above-described methods and apparatuses, it is believed that these results can be significantly improved. Specifically, it would be desirable to produce a mitral annuloplasty ring that can re-shape the mitral annulus in a way that will significantly repair the geometric configuration of the left ventricle wall beyond that which has been observed with undersized rings.

SUMMARY OF THE INVENTION

The present invention provides a number of annuloplasty rings for implantation in a mitral valve annulus that correct both the annulus and help mitigate the effects of congestive heart failure. In one aspect, the invention provides an annuloplasty ring that has a generally oval-shaped ring body defining an anterior portion, a posterior portion opposite the anterior portion, right and left sides between the anterior and posterior portions, and transition segments between the sides and the posterior portion. The ring body is oriented about a central axis having an upward direction and a downward direction, the downward direction corresponding to the direction of blood flow through the mitral valve annulus. The ring has, in plan view perpendicular to the central axis, a longer dimension along a major axis than a shorter dimension along a minor axis, and the posterior portion rises upward from the adjacent transition segments to an axial position higher than the highest axial position of the anterior portion.

Desirably, the posterior portion extends radially inward from the adjacent transition segments to a radial position along the minor axis that is closer to the central axis than an imaginary posterior projection in plan view of the sides toward each other. Preferably, the posterior portion extends radially inward from the adjacent transition segments to a radial position that is about 30-50% closer to the central axis than the imaginary posterior projection of the sides toward each other.

In accordance with a one embodiment of the present invention, the ring is substantially saddle-shaped with the sides curving upward between the anterior portion and adjacent transition segments. The right and left sides may rise to axial positions above the highest axial position of the anterior portion. The posterior portion rises upward from the adjacent transition segments to an axial position approximately equal to or above the highest axial positions of the right and left sides. Alternatively, the ring may be generally planar except for the posterior portion which rises to an elevated axial position.

In another embodiment, the sides and transition segments are generally curvilinear and the junctures between adjacent sides and transition segments are generally rounded. The posterior portion desirably also extends radially inward from the adjacent sides to a radial position along the minor axis that is closer (preferably about 30-50% closer) to the central axis than an imaginary posterior projection in plan view of the sides toward each other.

The ring body is preferably comprised of a material having a high modulus of elasticity that will substantially resist distortion when subjected to the stress imparted thereon when the ring is implanted in the mitral valve annulus of an operating human heart. For example, the ring can be comprised of a ceramic material such as Stellite, titanium, Elgiloy, graphite, ceramic, hardened plastics, composite, or Nitinol® materials. The annuloplasty ring may further comprise an outer sewing sheath surrounding the ring body, the sewing sheath being formed of a material that will permit the passage of sutures therethrough for securing to ring to a mitral annulus.

The present invention also provides a mitral annuloplasty ring comprising a ring body made of a material having a high modulus of elasticity that will substantially resist distortion when subjected to the stress imparted thereon when the ring is implanted in the mitral valve annulus of an operating human heart. The ring body is oriented about a central axis having an upward direction and a downward direction corresponding to the direction of blood flow through the mitral valve annulus, and has a posterior bow that extends both radially inward and axially upward. Desirably, ring body has an anterior portion, a posterior portion opposite the anterior portion, right and left sides between the anterior and posterior portions, and transition segments between the sides and the posterior portion. The ring body may be substantially saddle-shaped with the sides curving upward between the anterior portion and adjacent transition segments. In a preferred embodiment, a mid-section of the posterior portion bows upward from the adjacent transition segments to an axial position higher than the highest axial position of either of the right or left sides. Also, the right and left sides each may rise upward from the adjacent transition segments to an axial position above the highest axial position of the posterior portion.

DESCRIPTION OF THE PREFERRED EMBODIMENTS

Applicant has determined that congestive heart failure (CHF) and secondary mitral regurgitation (MR) can be addressed with a new generation mitral annuloplasty ring. The ring when implanted not only modifies the circumference of the mitral annulus as do existing annuloplasty rings, but it also elevates and/or reconfigures the posterior portion of the mitral annulus so as to mold and re-shape the geometry of the left ventricle.

The attached figures illustrate several exemplary embodiments of the annuloplasty ring of the present invention, which can be described as being continuous and having an anterior side, a posterior side and right and left sides. All of the sides are generally curvilinear with no specific demarcations to indicate abrupt transitions therebetween. Rather, smooth transitional sections between the adjacent sides provide curvilinear connections that give the ring a generally rounded (i.e., oval) configuration.

Figure 4A:
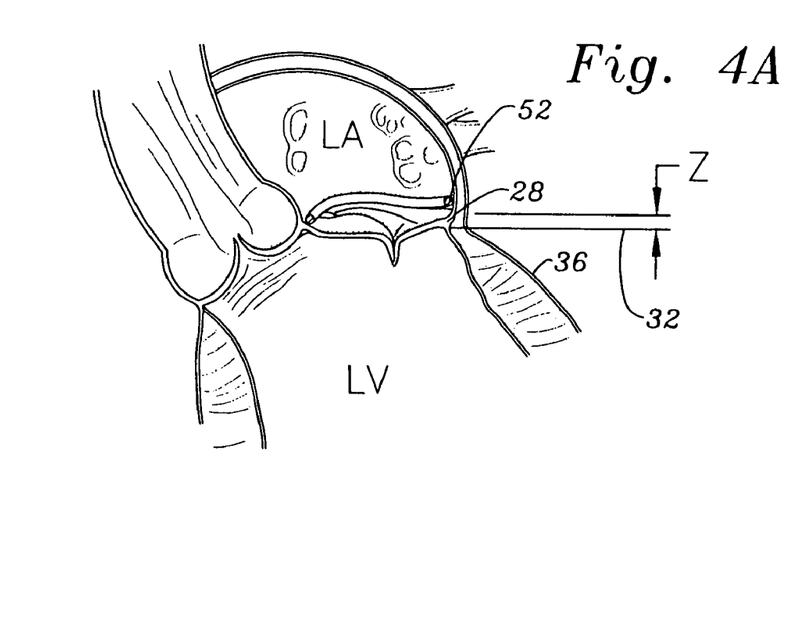
FIG. 4A is a cross-sectional view along an anterior-posterior plane through the left side of a heart illustrating the implantation of an annuloplasty ring of the present invention to restore the mitral valve to an over compensated position that will foster LV remodeling.
Figure 4B:
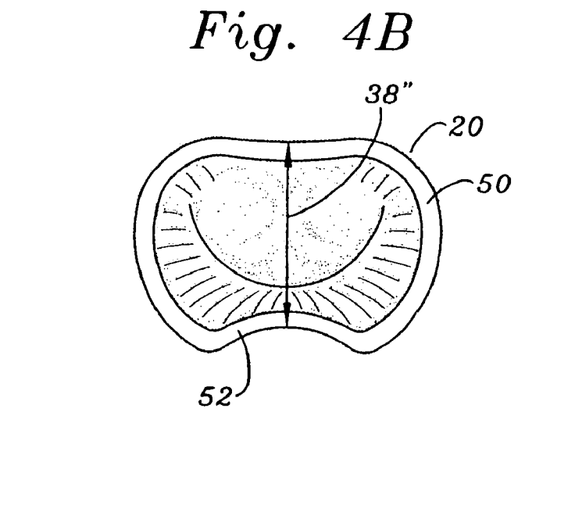
FIG. 4B is a plan view of the restored mitral valve of FIG. 4A.

With reference to FIGS. 4A and 4B, a first exemplary mitral annuloplasty ring 50 of the present invention is shown implanted in the mitral annulus 20. As seen in FIG. 4A, the posterior aspect 28 of the mitral annulus rises axially upward by a distance z from the datum plane 32 of the annulus when healthy. In addition, as seen in FIG. 4B, the anterior-posterior dimension 38 of the mitral annulus has been reduced by the annuloplasty ring 50. These two corrections to the mitral annulus are accomplished by a specially shaped posterior portion 52 of the annuloplasty ring 50, and because the ring is made relatively rigid. Because of the elevation of the posterior aspect 28 of the mitral annulus, the left ventricular wall 36 is molded and re-shaped, which helps mitigate some of the effects of CHF.

The degree to which a mid-section of the posterior portion 52 rises depends on multiple variables including specific patient pathology and the overall ring size, but it is projected that for applications in most adult sized hearts the preferable rise will be about 3-5 millimeters. Unlike prior annuloplasty rings, this configuration is not intended to follow the natural curvature of the mitral annulus. Rather, when the annuloplasty ring 50 is implanted in a mitral annulus, the "over-correcting" upward curvature of the ring 50 imparts a unique shape to the annulus that has the effect of molding and reshaping both the mitral annulus and the left ventricle. It is believed that this molding and reshaping of the geometry of the left ventricle will reduce the severity of CHF which in turn will reduce strain on the mitral valve and corresponding MR (and vice versa). In other words, this ring provides an annular solution to address ventricular pathology.

Figure 5:
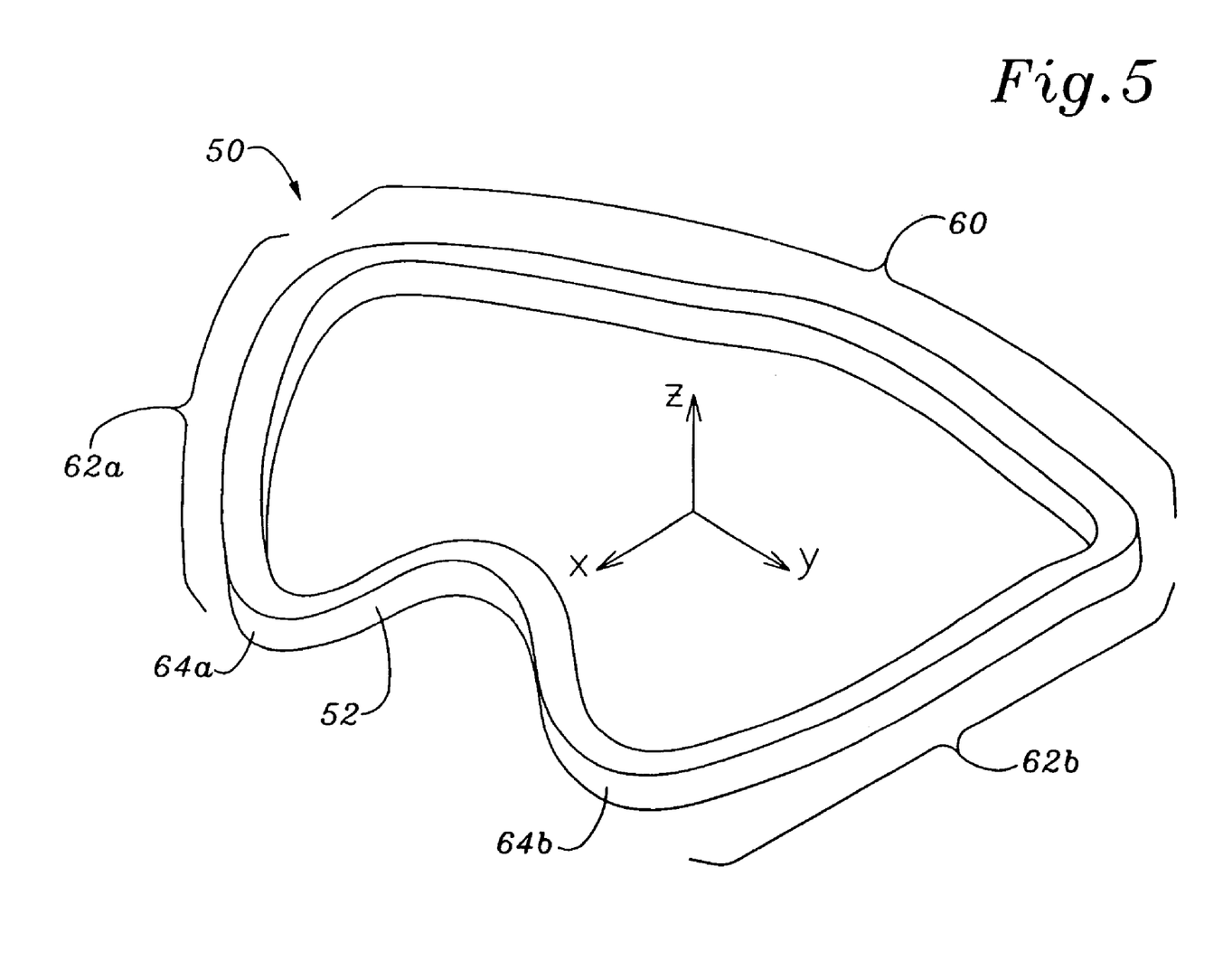
FIG. 5 is a perspective view of an inner support for an annuloplasty ring of the present invention.
Figure 6A:
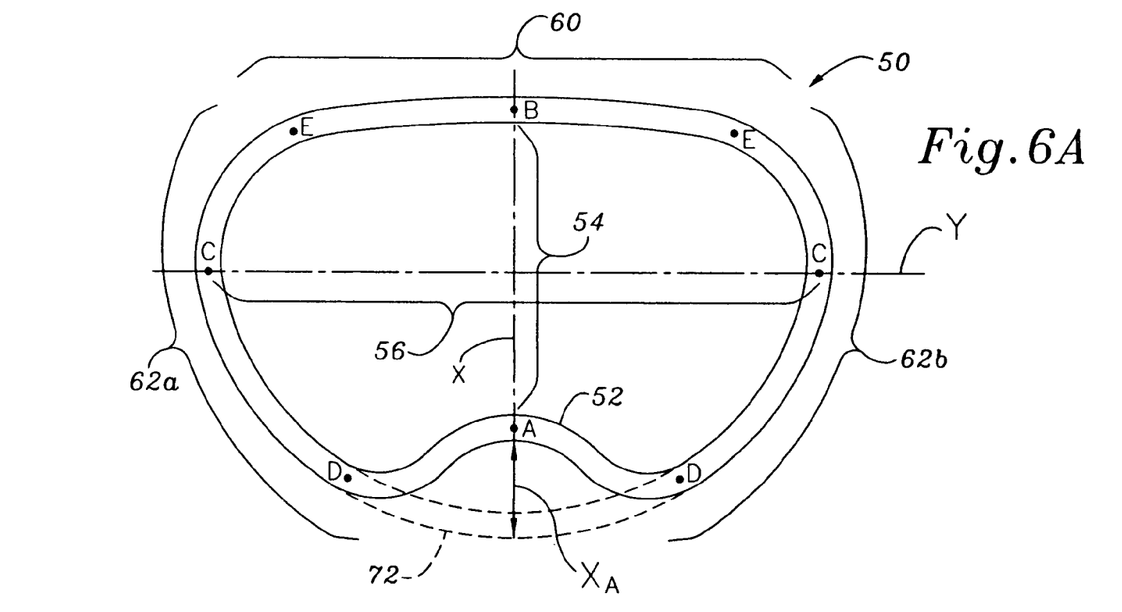
FIGS. 6A-6C are top plan, front elevational, and side elevational views, respectively, of the annuloplasty ring of FIG. 5.
Figure 6B:
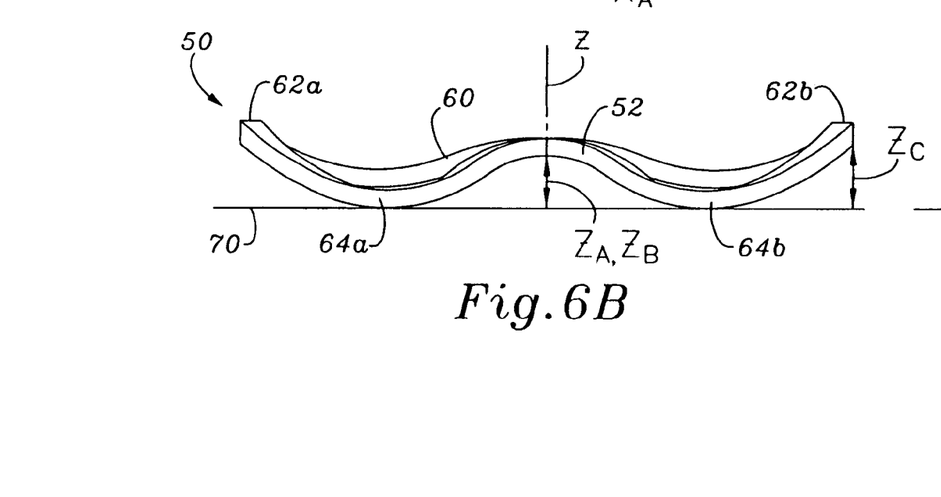
Figure 6C:
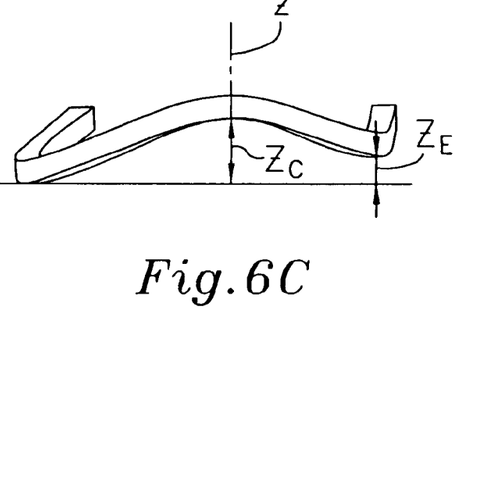

The exemplary annuloplasty ring 50 of FIGS. 4A and 4B is shown in more detail in FIGS. 5-6C. For purpose of orientation, FIG. 5 illustrates orthogonal axes wherein the Z-axis lies along of the axis of blood flow through the ring when implanted, and the X- and Y-axes generally define the datum plane 32 as mentioned above. It will further be understood that the positive Z direction illustrated in FIG. 5 is the "upward" direction, the negative Z direction is the "downward" direction, and the ring is designed to be implanted in a mitral annulus such that blood will flow in the downward direction.

As seen in FIG. 6A, the X-axis extends across the ring in the anterior-posterior direction illustrating a minor axis dimension 54. The X-axis typically lies in a plane of symmetry of the ring 50 such that the left side and right side are identical. The Y-axis extends across the long dimension of the ring 50 such that a major axis dimension 56 is defined.

As with many conventional rings, the ratio of the minor axis dimension 54 to the major axis dimension 56 is about 3:4. Although not geometrically precise, such a ring configuration may be considered oval or elliptical.

As seen in FIG. 6A, the annuloplasty ring 50 includes the specially shaped posterior portion 52, an anterior portion 60, and a pair of generally symmetric side portions 62a, 62b. As can be seen from the perspective of FIG. 5, two relatively sharply curved transition segments 64a, 64b join either side of the posterior portion 52 to the side portions 62a, 62b.

With reference also to FIGS. 6B and 6C, the relative elevations in the Z-axis of the various portions of the ring 50 are shown in FIG. 5. FIG. 6B shows that the transition segments 64a, 64b are located at the lowest points about the ring 50 when in its "horizontal" orientation over an X-Y reference plane 70. A mid-section of the shaped posterior portion 52 arcs upward between the transition segments 64a, 64b and has its highest point on the X-Z plane. Likewise, the two side portions 62a, 62b arc gently upward from the respective transition segments 64a, 64b and then gradually curve downward into a blended transition with the anterior portion 60. As seen in the background of FIG. 6B, the anterior portion 60 exhibits a slight upward bow centered along the X-Z plane, and preferably rises to the same height as the shaped posterior portion 52. The overall contour of ring 50 around its periphery is undulating or serpentine. If a three-dimensional surface were drawn across the open middle of the ring to conform as much as possible to the periphery of the ring 50, that surface would be somewhat saddle-shaped with upward bows along the Y-Z and X-Z planes. (To further illustrate the overall shape of the ring 50, it somewhat resembles a molded potato chip sold under the Pringles brand.) The extent of upward curvature for the ride and left side portions 62a, 62b may reach as high, or higher, than that of the posterior portion 52, but do not necessarily need to extend this high. This too will depend on multiple factors including patient pathology.

The difference in elevation between the shaped posterior portion 52 and the adjacent transition segments 64a, 64b is shown at $z_A$ in FIG. 6B. The subscript "A" refers to the point A around the ring 50 periphery as indicated in FIG. 6A. The midpoint of the anterior portion 60 is denoted at B, while the points along the side portions 62a, 62b that lie on the Y-Z plane are denoted at C. The lowest points in the transition segments 64a, 64b are denoted at D, while lowest points along the anterior portion 60 are denoted at E. The elevational at each of these points is represented as $z_A$, $z_B$, $z_C$, $z_D$, and $z_E$. It should be noted also that the elevations are as measured to the bottom of the ring 50, although the thickness of the ring means that the overall height is somewhat greater. When viewed with reference to the plane 70, $z_D$ is at zero. In this embodiment, $z_A = z_B = z_C$, but, as will be described below, $z_A$ may be substantially greater than either $z_B$ or $z_C$, and $z_B$ is desirably larger than $z_C$.

FIGS. 5-6C also illustrate a second aspect of the present invention, namely that a mid-section of the posterior portion 52 extends inward to a radial position that is closer to the central axis than if the right and left side portions 62a, 62b projected smoothly toward one another. This too results in a reshaping effect on the mitral annulus, which in turn reshapes the left ventricle geometry.

With reference again to FIG. 6A, a phantom projection or extension 72 of the two side portions 62a, 62b is indicated. This arcuate imaginary extension 72 has been drawn to illustrate the inward bow of the shaped posterior portion 52. That is, the posterior portion 52 diverges inward from this imaginary ring projection, which represents conventional oval-shaped rings of the prior art. Specifically, the posterior portion 52 bows inward at point A a distance indicated as $x_A$. As with the axial correction noted above, the degree to which the posterior portion 52 extends inward will depend on multiple variables, but it is preferable that the innermost position of the posterior side be about 30-50% closer to the central axis than the arcuate imaginary extension 72. Of course, the distance $x_A$ varies depending on the overall size of the ring 50.

With reference again to FIGS. 4A and 4B, the effect of the inward and upward posterior portion 52 of the ring 50 as implanted can be seen. In FIG. 4A, the posterior portion 52 causes the posterior portion 28 of the mitral annulus 20 to elevate above the datum plane 32 the distance z. This shift in the mitral annulus 28 places the left ventricular wall 36 in greater tension than normal and helps re-shape and recondition that wall to help rectify the detrimental effects of CHF. Furthermore, not only does the ring 50 elevate the posterior portion 28 of the mitral annulus 20, but it also pulls that side of the annulus radially inward, as indicated in FIG. 4B. The anterior-posterior dimension 38" is shown reduced from its normal dimension (the normal dimension is essentially represented in FIG. 3B as 38').

Figure 7A:
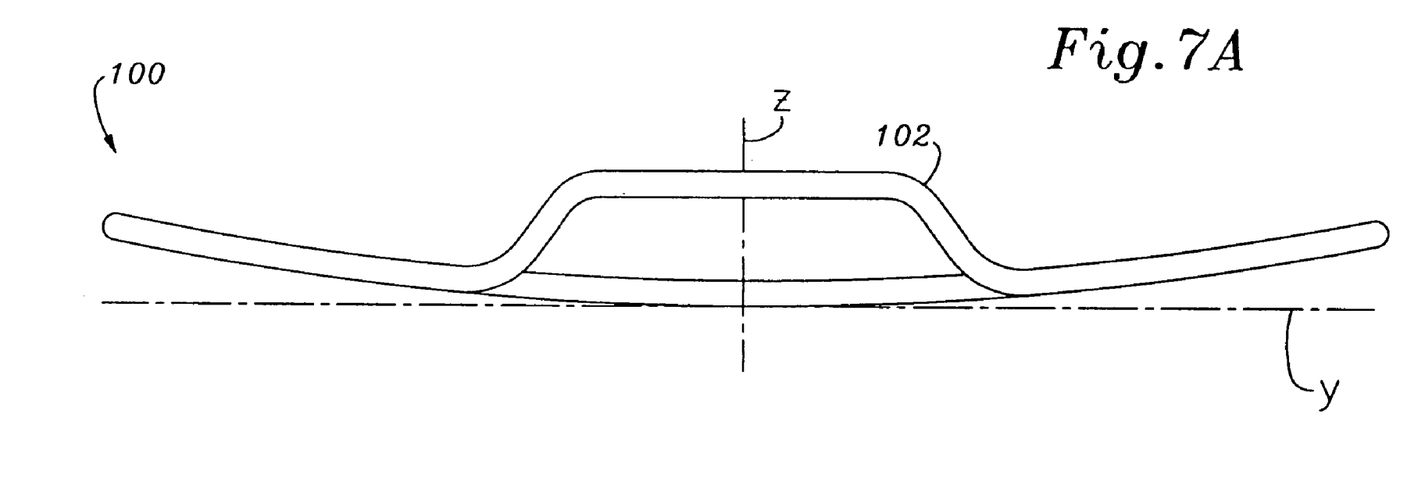
FIGS. 7A-7B are front and side elevational views, respectively, of an alternative annuloplasty ring of the present invention.
Figure 7B:
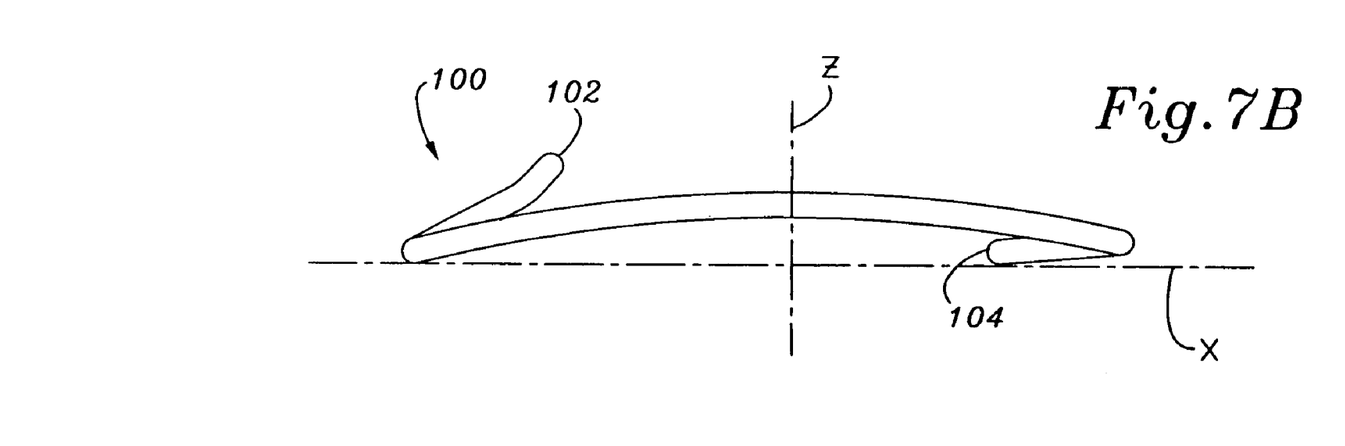

FIGS. 7A and 7B show front and side elevational views of an alternative annuloplasty ring 100 of the present invention that shares some of features of the annuloplasty ring 50 described above. For example, the overall contour of ring 100 bows upward along the Y-Z plane as indicated in FIG. 7B, and a mid-section of a posterior portion 102 is both upwardly (see FIG. 7A) and inwardly (see FIG. 7B) displaced from an imaginary continuation of the side portions of the ring. As seen best from the front in FIG. 7A, the ring 100 does not have a serpentine configuration as with the earlier-described ring 50, instead the profile from the front lies generally in a single arc with the posterior portion 102 elevated relatively suddenly therefrom.

FIG. 7B shows that the middle segment 104 of the anterior side of the ring also bows inwardly from the adjacent sides to a radial position along the X-axis that is closer to the central axis than an imaginary anterior projection in plan view of the adjacent sides toward each other. The inward curve of the anterior segment 104 further reduces the dimension of the repaired annulus in the anterior-posterior plane, and contributes to pulling the posterior aspect of the annulus inward and at the same time conditioning the left ventricular wall.

Figure 8A:
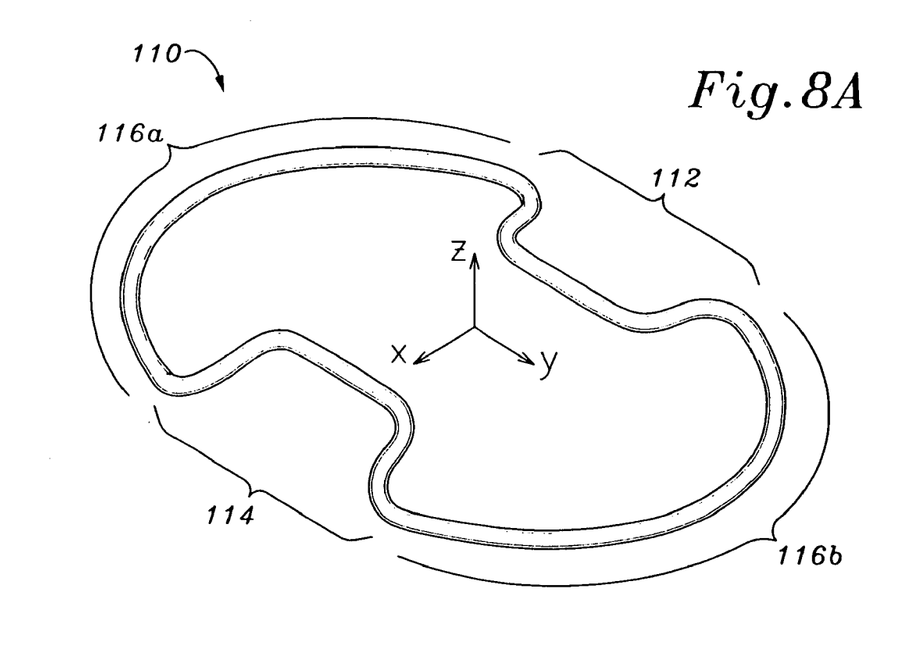
FIGS. 8A-8C are perspective, front elevational, and side elevational views of a further alternative annuloplasty ring of the present invention.
Figure 8B:
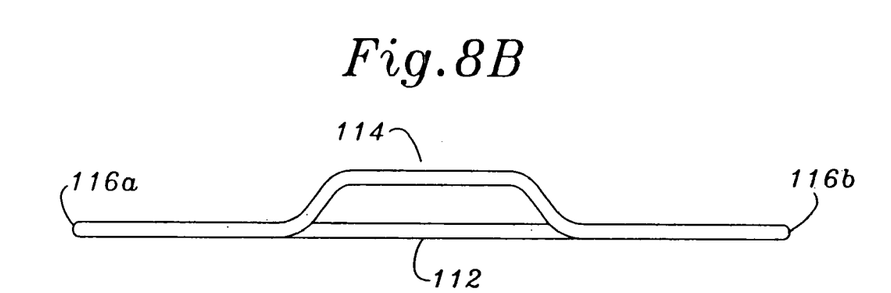
Figure 8C:
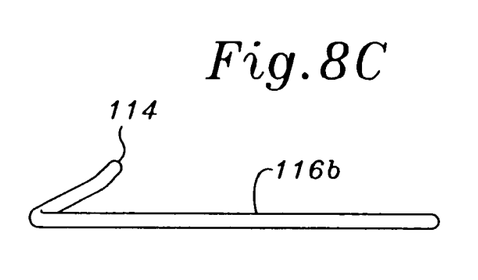

FIGS. 8A-8C illustrate a generally planar annuloplasty ring 110 of the present invention having an anterior portion 112, an opposing posterior portion 114, and left and right sides 116a, 116b. A mid-section of a posterior portion 114 is substantially the same as the posterior portion 102 in FIGS. 7A and 7B such that it bows inward and upward. As in the earlier version, the anterior portion 112 bows inwardly, although the entire periphery of the ring 110 except for the posterior portion 114 lies in a plane.

Figures 9A, 9B, 9C, 9D:
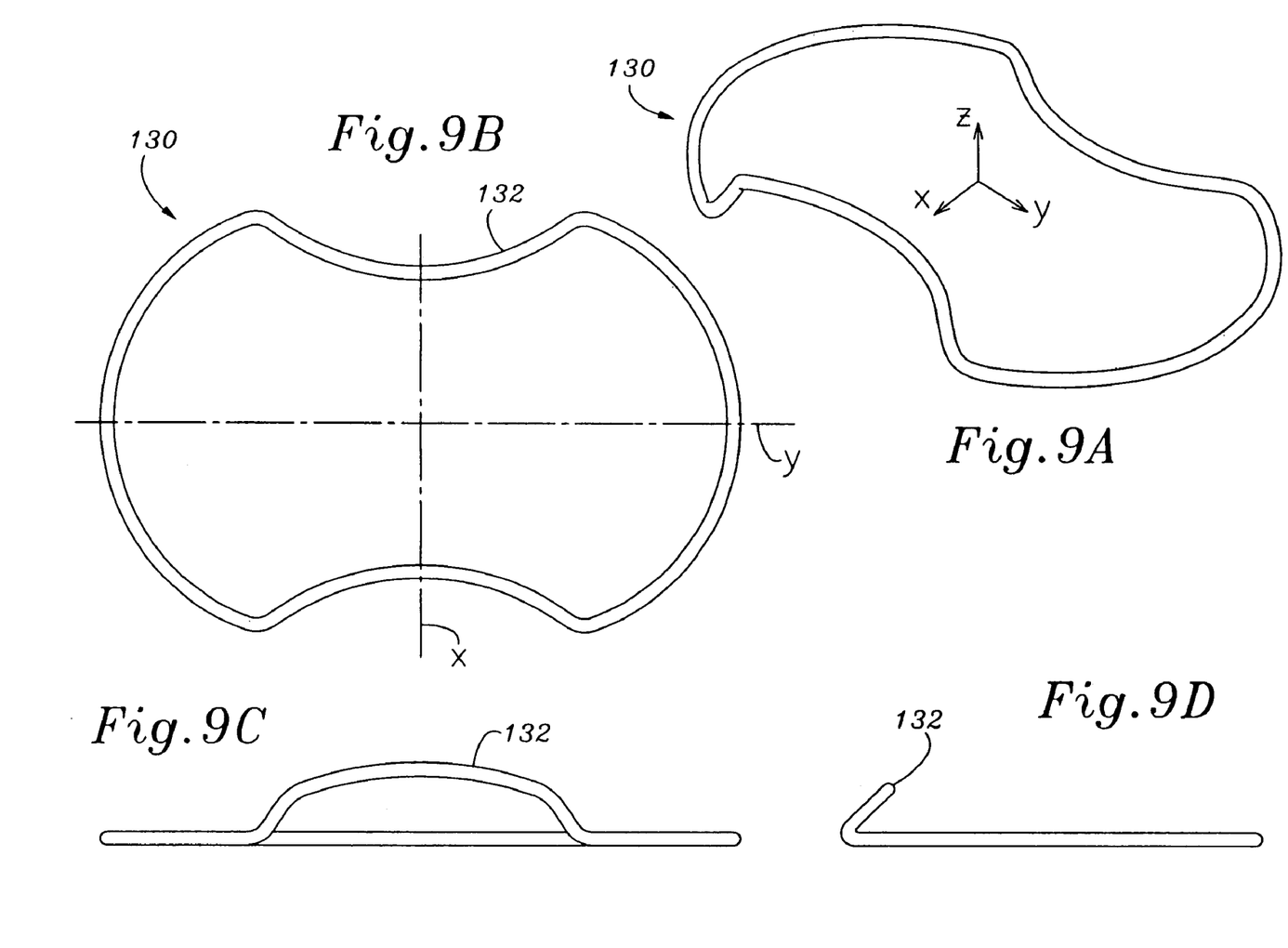
FIGS. 9A-9D are various views of a further exemplary annuloplasty ring of the present invention.
Figures 10A, 10B, 10C, 10D:
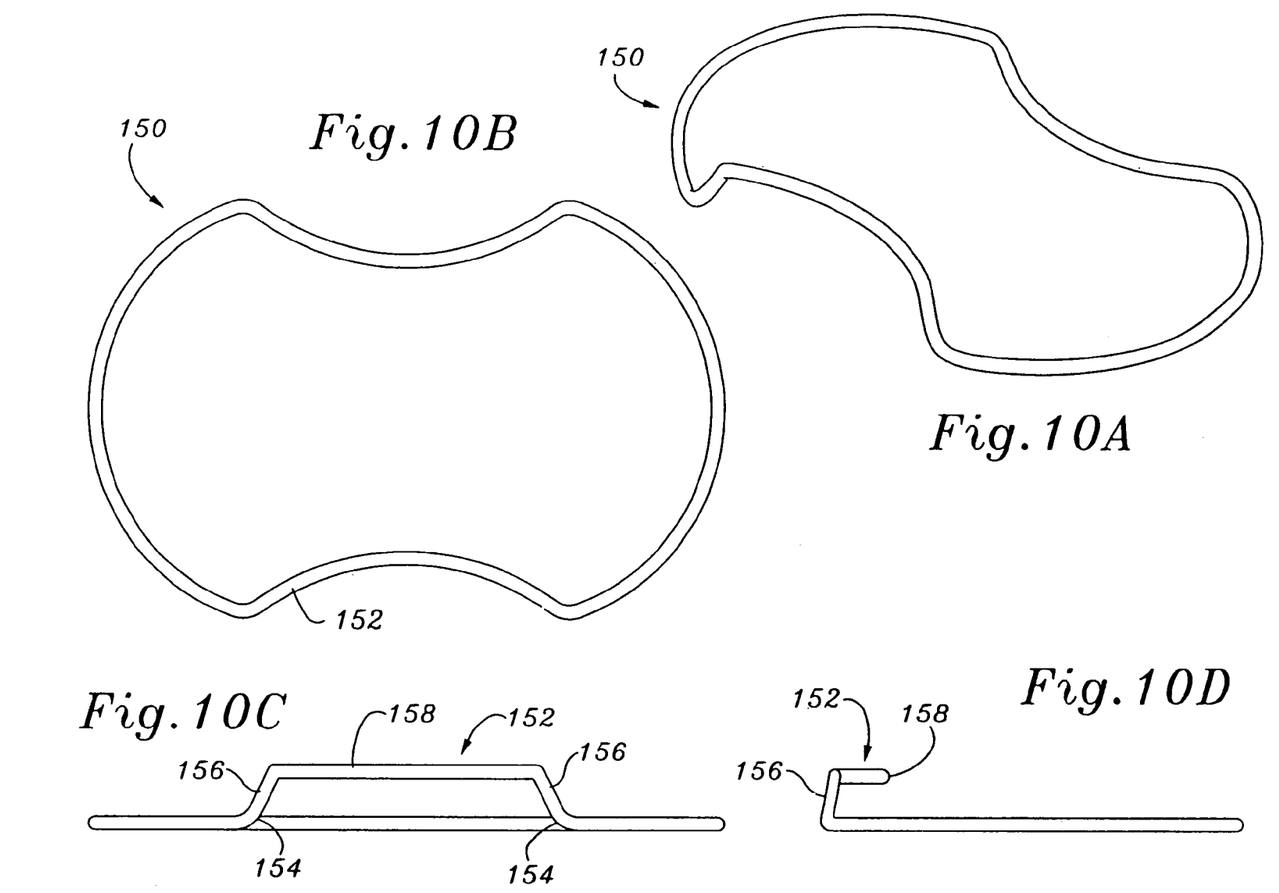
FIGS. 10A-10D are various views of a still further exemplary annuloplasty ring of the present invention.

FIGS. 9A-9D illustrate an alternative annuloplasty ring 130 of the present invention that, as viewed in plan view in FIG. 9B, is symmetric both about the X-Z plane and the Y-Z plane. The ring 130 is not symmetric in elevation, as seen in FIGS. 9C and 9D, wherein a mid-section of a posterior portion 132 rises upward and curves inward. As with the embodiment of FIGS. 8A-8C, the entire ring 130 lies in a plane except for the posterior portion 132. Again, the particular configuration of the posterior portion 132 helps re-shape the mitral annulus and recondition the left ventricular wall. Moreover, an anterior portion 132 also bows inward to help reduce the size of the mitral annulus in the anterior-posterior direction. As explained above, the term "bows inward" refers to the diversion of the particular portion from an imaginary curve that would continue the oval peripheral plan view of the ring.

FIGS. 10A-10D show another ring 150 the present invention that is nearly identical to the ring shown in FIGS. 9A-9D, except for a posterior portion 152. As seen best in FIGS. 10C and 10D, a mid-section of the posterior portion 152 rises at sharp transitions 154 from the rest of the ring 150 which is planar. Rather than a gentle upward and inward curvature, a short upward segment 156 connects a middle, inwardly curved segment 158 to each of the transitions 154. This embodiment of the ring 150 thus illustrates that specially shaped portions around the periphery do not necessarily have to join with the remainder of the ring in gentle blended curves.

Figure 11A:
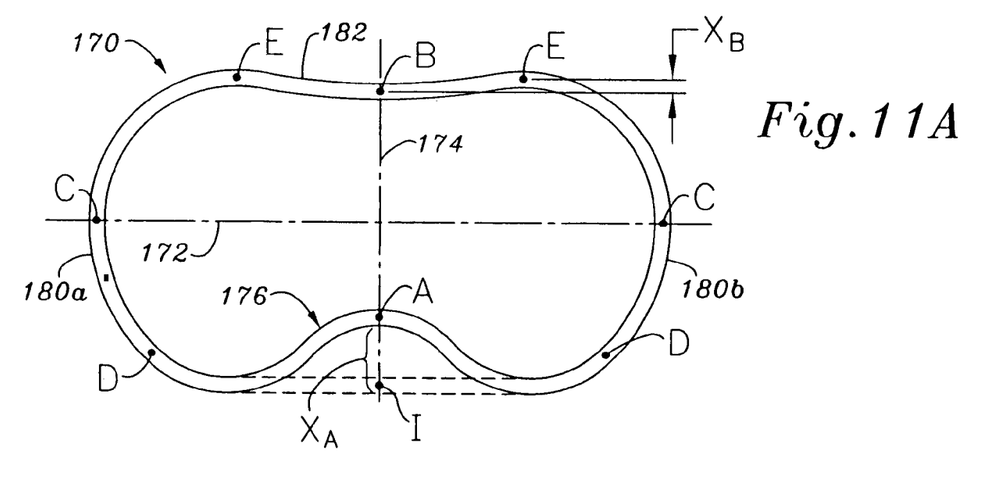
FIGS. 11A-11C are various views of another exemplary annuloplasty ring of the present invention.
Figure 11B:
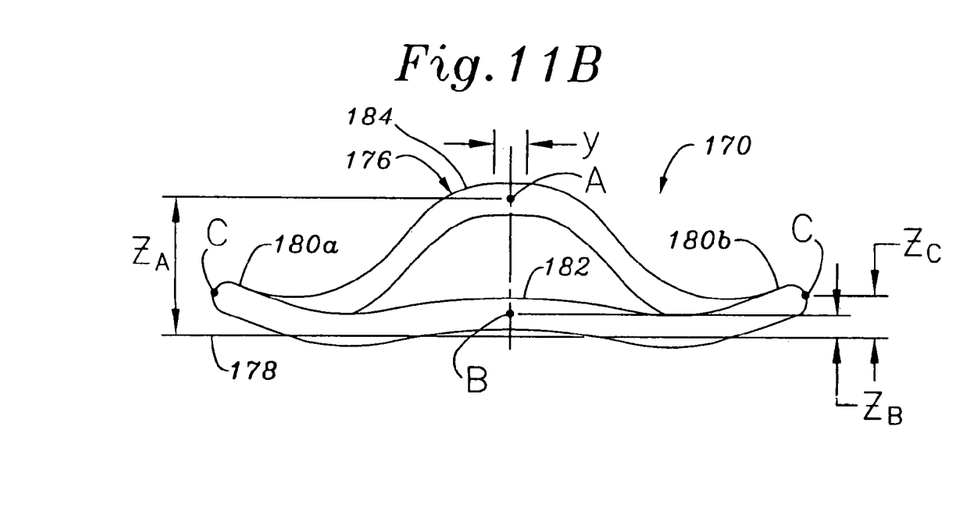
Figure 11C:
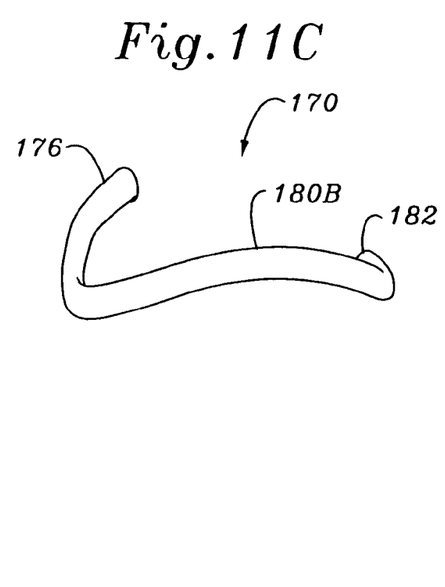

FIGS. 11A-11C are plan, front elevational, and side elevational views, respectively, of a still further annuloplasty ring 170 that is generally oval-shaped about a major axis 172 and a minor axis 174. The points A, B, C, D and E are located in the same places as described above with respect to FIG. 6A-6C. A mid-section 176 of a posterior portion of the ring 170 bows upward and inward. The elevation $z_A$ above a datum plane 178 is seen in FIG. 11B, while the magnitude of inward bow $x_A$ is seen in FIG. 11A. The sides 180a, 180b also bow upward a distance $z_C$ as indicated in FIG. 11B. Finally, an anterior portion 182 bows upward a distance $z_B$ and inward a distance $x_B$. In this embodiment, $z_A \neq z_B \neq z_C$. The mid-section 176 forms a plateau 184 in the Z-direction centered about the minor axis 174 and having a dimension y as seen in FIG. 11B. The dimension y is desirably about 2 mm. This plateau 184 helps prevent kinking of a tubular fabric or other suture-permeable covering over the posterior portion because of the greater upward and inward bow in comparison to other rings described herein.

Exemplary dimensions for a 28 mm ring 170 include the following relations:

$0 < z_B \leq z_A$, and preferably,
$0.10\, z_A \leq z_B \leq 0.20\, z_A$, and more preferably,
$z_B = $ about $0.14\, z_A$.

Furthermore:

$z_C > z_B$, and,
$0 < z_C \leq z_A$, and preferably,
$0.20\, z_A \leq z_C \leq 0.40\, z_A$, and more preferably,
$z_C = $ about $0.28\, z_A$.

Finally, $3\text{ mm} < z_A \leq 8\text{ mm}$, and preferably,
$z_A = $ about 7 mm.

These relations and exemplary dimensions may be suitable for all sizes of rings, or may be scaled up or down proportionally.

The inward bow $x_A$ is desirably about 40% of the distance along the minor axis from point B to point I regardless of the ring size. Point I is the location of the mid-point of an imaginary posterior projection in plan view of the sides 180a, 180b toward each other. The anterior inward bow $x_B$ is desirably about 1 mm.

The ideal degree to which the posterior and/or anterior sides are molded inward and upward according this invention depend on multiple factors. Preferably however, these features will be exaggerated to an extent that the mitral annulus is "over-corrected." In other words, a important factor of this invention is that the mitral annulus not be just repaired to its natural, pre-diseased state, but that the annulus actually be reduced past that point to an extent that will significantly affect the geometry of the left ventricle. Initial studies suggest that the inward and/or upward corrections for the posterior side be about 30-50% beyond that which would bring the annulus to its pre-diseased state.

The annuloplasty rings herein are desirably made of a single inner member as illustrated, covered with a suture-permeable outer layer. As opposed to flexible annuloplasty rings that are designed simply to reduce the circumference of the mitral annulus, the annuloplasty ring of the present invention must be quite stiff. It must substantially retain its shape in opposition to the stresses that will be imparted by muscles of the heart through out each beating cycle. Accordingly, this ring must be made from a material having a relatively high modulus of elasticity. For example, the inner member as shown may be machined or molded of Stellite, polished, and then covered with a polyterapthalate fabric. Alternatively, an intermediate silicone sleeve around the inner member may be used. Stellite provides a desired rigidity to best facilitate reshaping of the annulus and left ventricle, although more commonly used materials such as titanium, Elgiloy, graphite, ceramic, hardened plastics, or Nitinol® may be substituted.

The ring also preferably includes an outer sewing sheath that permits it to be sutured into the mitral annulus. The sewing sheath should be sufficiently porous and/or flexible to permit sutures to be passed therethrough, but it must not be so flexible as to counteract the stiffness requirements discussed above. Because the ring will be under such loads, it will also be necessary to insert more sutures in the sewing sheath than for more flexible rings (to reduce the loads on individual sutures). For example, if traditional rings require in the neighborhood of 8 to 10 stitches around the circumference, the present annuloplasty ring might require as many as 20-30 or more.

It will be understood by those of skill in the art that the embodiments described above can be incorporated individually or in combination. While each aspect will have the desired effect of and reshaping the mitral annulus and left ventricle, it is the re-shaping of the posterior side that will have the greatest effect of molding and re-shaping the left ventricle. The aspect of extending the anterior side radially inward will preferably not be used unless the posterior side has also been configured as described herein.

It will also be readily apparent that re-shaping the mitral valve annulus with the present annuloplasty ring will cause the mitral leaflets to coapt in a new location. However, those of skill in the art will recognize that this slight realignment of the leaflets is acceptable, and often even preferable.

It will be appreciated by those of skill in the relevant art that various modifications or changes may be made to the examples and embodiments of the invention described in this provisional application, without departing from the intended spirit and scope of the invention. In this regard, the particular embodiments of the invention described herein are to be understood as examples of the broader inventive concept disclosed in this application.

What is claimed is:

1. A method of implanting an annuloplasty ring in a mitral valve annulus having an anterior aspect and a posterior aspect, the annulus having a dilated pathology symptomized by lengthening of the anterior-posterior dimension and a subsequent loss of coaptation between the posterior and anterior leaflets thus causing mitral regurgitation, the annulus further exhibiting a drop of the posterior aspect and consequent relaxation of the posterior muscle wall of the left ventricle, the method comprising:

providing a generally oval-shaped annuloplasty ring having an anterior portion adapted to be implanted on the anterior aspect of the mitral valve annulus, a posterior portion opposite the anterior portion adapted to be implanted on the posterior aspect of the mitral valve annulus, right and left sides between the anterior and posterior portions, and transition segments between the sides and the posterior portion;

wherein the annuloplasty ring is oriented about a central axis having an upward direction and a downward direction, the downward direction corresponding to the direction of blood flow through the mitral valve annulus, the ring having in plan view perpendicular to the central axis a longer dimension along a major axis than a shorter dimension along a minor axis, the ring posterior portion having an upward bow that rises upward to an axial position higher than the remainder of the ring; and, securing the annuloplasty ring with the anterior portion against the annulus anterior aspect and the posterior portion against the annulus posterior aspect so that the ring posterior portion elevates the annulus posterior aspect and re-shapes the geometry of the left ventricle.

2. The method of claim 1, wherein the posterior portion extends radially inward from the adjacent transition segments to a radial position along the minor axis that is closer to the central axis than an imaginary posterior projection in plan view of the sides toward each other, the method including reconfiguring the annulus accordingly.

3. The method of claim 1, wherein the ring is substantially saddle-shaped with the sides curving upward between the anterior portion and adjacent transition segments, the method including reconfiguring the annulus accordingly.

4. The method of claim 1, wherein the ring is generally planar except for the posterior portion, the method including reconfiguring the annulus accordingly.

5. The method of claim 1 wherein the sides and transition segments are generally curvilinear and the junctures between adjacent sides and transition segments are generally rounded, the method including reconfiguring the annulus accordingly.

6. The method of claim 1, wherein the posterior portion extends radially inward from the adjacent sides to a radial position along the minor axis that is closer to the central axis than an imaginary posterior projection in plan view of the sides toward each other, the method including reconfiguring the annulus accordingly.

7. The method of claim 1, wherein the ring body is comprised of a material having a high modulus of elasticity that will substantially resist distortion when subjected to the stress imparted thereon when the ring is implanted.

8. A method of correcting a mitral valve annulus having a dilated pathology symptomized by lengthening of dimension between an anterior aspect and a posterior aspect thereof, and a subsequent loss of coaptation between posterior and anterior leaflets thus causing mitral regurgitation, the annulus further exhibiting a drop of the posterior aspect and consequent relaxation of a posterior muscle wall of the left ventricle, the method comprising:

providing an annuloplasty ring made of a material having a high modulus of elasticity that will substantially resist distortion when subjected to the stress imparted thereon when the ring is implanted in the mitral valve annulus of an operating human heart, the annuloplasty ring having an anterior portion and a posterior portion with an upward bow; and, securing the annuloplasty ring with the anterior portion against the annulus anterior aspect and the posterior portion against the annulus posterior aspect so that the ring posterior portion elevates the annulus posterior aspect above its normal elevation and consequently re-shapes the geometry of the left ventricle.

9. The method of claim 8, wherein the annuloplasty ring is comprised of a ceramic material.

10. The method of claim 9, wherein the annuloplasty ring is comprised of Stellite.

11. A method of implanting an annuloplasty ring in a mitral valve annulus having an anterior aspect and a posterior aspect, the annulus having a dilated pathology symptomized by lengthening of the anterior-posterior dimension and a subsequent loss of coaptation between the posterior and anterior leaflets thus causing mitral regurgitation, the method comprising:

providing an annuloplasty ring made of a material having a high modulus of elasticity that will substantially resist distortion when subjected to the stress imparted thereon when the ring is implanted in the mitral valve annulus of an operating human heart, wherein the ring is oriented about a central axis having an upward direction and a downward direction, the downward direction corresponding to the direction of blood flow through the mitral valve annulus, the ring having a posterior portion that extends both radially inward and axially upward from the remainder of the ring; and securing the annuloplasty ring with the anterior portion against the annulus anterior aspect and the posterior portion against the annulus posterior aspect so that the ring posterior portion elevates and pulls radially inward the annulus posterior aspect.

12. The method of claim 11, wherein the ring body has an anterior portion, a posterior portion opposite the anterior portion, right and left sides between the anterior and posterior portions, and transition segments between the sides and the posterior portion, and wherein the ring body is substantially saddle-shaped with the sides curving upward between the anterior portion and adjacent transition segments, the method including reconfiguring the annulus accordingly.

13. The method of claim 12, wherein a mid-section of the posterior portion bows upward from the adjacent transition segments to an axial position higher than the highest axial position of either of the right or left sides, the method including reconfiguring the annulus accordingly.

14. The method of claim 12, wherein the right and left sides each rise upward from the adjacent transition segments to an axial position above the highest axial position of the posterior portion, the method including reconfiguring the annulus accordingly.

15. The method of claim 11, wherein the ring body is generally planar except for the upwardly bowed posterior portion, the method including reconfiguring the annulus accordingly.

16. The method of claim 11, wherein the ring body has an anterior portion, a posterior portion opposite the anterior portion, right and left sides between the anterior and posterior portions, and transition segments between the sides and the posterior portion, and wherein the posterior portion extends radially inward from the adjacent transition segments to a radial position along the minor axis that is closer to the central axis than an imaginary posterior projection in plan view of the sides toward each other, the method including reconfiguring the annulus accordingly.

17. The method of claim 11, wherein the ring body has an anterior portion, a posterior portion opposite the anterior portion, right and left sides between the anterior and posterior portions, and transition segments between the sides and the posterior portion, and wherein the posterior portion extends radially inward from the adjacent sides to a radial position along the minor axis that is closer to the central axis than an imaginary posterior projection in plan view of the sides toward each other, the method including reconfiguring the annulus accordingly.

18. A method of implanting an annuloplasty ring in a mitral valve annulus having an anterior aspect and a posterior aspect, the annulus having a dilated pathology symptomized by lengthening of the anterior-posterior dimension and a subsequent loss of coaptation between the posterior and anterior leaflets thus causing mitral regurgitation, the method comprising:

providing an annuloplasty ring made of a material having a high modulus of elasticity that will substantially resist distortion when subjected to the stress imparted thereon when the ring is implanted in the mitral valve annulus of an operating human heart, the annuloplasty ring having an anterior portion and a posterior portion that extends both radially inward and axially upward from the remainder of the ring; and, securing the annuloplasty ring with the anterior portion against the annulus anterior aspect and the posterior portion against the annulus posterior aspect so that the ring posterior portion elevates and pulls radially inward the annulus posterior aspect and corrects the mitral regurgitation.

19. The method of claim 18, wherein the annuloplasty ring is comprised of a ceramic material.

20. The method of claim 19, wherein the annuloplasty ring is comprised of Stellite.

* * * * *